(12) United States Patent
Veillette (10) Patent No.: US 8,812,110 B2
(45) Date of Patent: Aug. 19, 2014

(54) IMPLANTABLE MEDICAL DEVICE

(75) Inventor: Benoit Veillette, Portland, OR (US)

(73) Assignee: Biotronik CRM Patent AG, Baar (CH)

( * ) Notice: Subject to any disclaimer, the term of this patent is extended or adjusted under 35 U.S.C. 154(b) by 1685 days.

(21) Appl. No.: 12/045,130

(22) Filed: Mar. 10, 2008

(65) Prior Publication Data

US 2009/0228062 A1  Sep. 10, 2009

(51) Int. Cl.
*A61N 1/08* (2006.01)
*A61N 1/372* (2006.01)
*A61N 1/368* (2006.01)

(52) U.S. Cl.
CPC .......... *A61N 1/37247* (2013.01); *A61N 1/3682* (2013.01)
USPC ................................. 607/32; 607/30; 607/60

(58) Field of Classification Search
USPC ................................. 607/30, 32, 60
See application file for complete search history.

(56) References Cited

U.S. PATENT DOCUMENTS

| 5,697,884 | A  | * | 12/1997 | Francischelli et al. | 600/17 |
| 7,181,285 | B2 | * | 2/2007  | Lindh et al. | 607/30 |
| 2003/0045909 | A1 | * | 3/2003 | Gross et al. | 607/9 |
| 2008/0027337 | A1 | * | 1/2008 | Dugan et al. | 600/508 |
| 2008/0288023 | A1 | * | 11/2008 | John | 607/59 |

* cited by examiner

*Primary Examiner* — Tammie K Heller
(74) *Attorney, Agent, or Firm* — ARC IP Law, PC; Joseph J. Mayo (57) ABSTRACT

An implantable medical device (IMD) that can be wirelessly connected to user interface by which a patient can enter values of selected control parameters for controlling the IMD whereas other control parameters are not accessible via said user interface and can only be modified by a physician or other authorized personnel.

17 Claims, 4 Drawing Sheets

IMPLANTABLE MEDICAL DEVICE

BACKGROUND OF THE INVENTION

1. Field of the Invention

The invention relates to an implantable medical device in general and to an implantable heart stimulator in particular.

The implantable heart stimulator preferably is an implantable pacemaker or an implantable cardioverter/defibrillator (ICD), or a device for cardiac resynchronization (CRT-D).

2. Description of the Related Art

Heart stimulators such as cardiac pacemakers are medical devices, usually implantable, that can be connected to or that are permanently connected to electrode leads for delivery of electrical stimulations pulses to the tissue (myocardium) of a human heart. Dual chamber pacemakers are capable of generating stimulation pulses for the atrium and the ventricle of a human heart. Biventricular pacemakers usually are capable to stimulate at least three chambers of a human heart that is the right atrium, the right ventricle and the left ventricle.

In a dual chamber pacemaker, this is usually realized by placing electrodes in both the right atrium and right ventricle of the heart.

In a demand-type pacemaker these electrodes are coupled through intravenous and/or epicardial leads to sense amplifiers housed in an implanted pacemaker. Electrical activity occurring in these chambers can thus be sensed. When electrical activity is sensed, the pacemaker assumes that a depolarization following a contraction of the indicated chamber has occurred. If no electrical activity is sensed within a prescribed time interval, typically referred to as an atrial or ventricular escape interval, then a pulse generator, also housed within the pacemaker housing, generates a stimulation pulse that is delivered to the indicated chamber, usually via the same lead as is used for sensing.

Separate stimulation pulse generators are usually provided for each heart chamber (atrium or ventricle) to be stimulated.

A control unit triggers the generation of a respective atrial or ventricular stimulation pulse according to a pre-programmed, variable timing regime in order to provide for adequate timing of the stimulation pulses.

A stimulation pulse to the myocardium may cause a contraction of a respective heart chamber, if the myocardium of that chamber is not in a refractory state and if the stimulation pulse intensity is above the stimulation threshold of said myocardium. A sub-threshold stimulation pulse will not cause a cardiac contraction even if delivered to the myocardium in its non-refractory state.

Depending on the mode of operation, a pacemaker only delivers a stimulation pulse (pacing pulse) to a heart chamber (atrium or ventricle) if needed, that is, if no natural excitation of that chamber occurs. Such mode of operation is called an inhibited or demand mode of operation since the delivery of a stimulation pulse is inhibited if a natural excitation of the heart chamber is sensed within a predetermined time interval (usually called escape interval) so the heart chamber is only stimulated if demanded.

In a demand mode, the pacemaker monitors the heart chamber to be stimulated in order to determine if a cardiac excitation (heartbeat) has naturally occurred, such natural (non-stimulated) excitation, also referred to as "intrinsic" or "signs" cardiac activity, are manifested by the occurrence of recognizable electrical signals that accompany the depolarization or excitation of a cardiac muscle tissue (myocardium). The depolarization of the myocardium is usually immediately followed by a cardiac contraction. For the purpose of the present application, depolarization and contraction may be considered as simultaneous events and the terms "depolarization" and "contraction" are used herein as synonyms.

In order to monitor the heart chamber and thus to determine whether or not a natural contraction of a heart chamber has occurred a pacemaker has a sensing stage which during operation of the pacemaker is connected to an electrode placed in a respective heart chamber. A natural contraction of a heart chamber can be detected by evaluating electrical potentials sensed by such sensing electrode. In the sensed electrical signal the depolarization of an atrium muscle tissue is manifested by occurrence of a signal known as "P-wave". Similarly, the depolarization of ventricular muscle tissue is manifested by the occurrence of a signal known as "R-wave". A P-wave or an R-wave represents an atrial event or a ventricular event, respectively, in the further course of this application.

In a demand mode of operation, the pacemaker monitors the heart for the occurrence of P-waves and/or R-waves. If such signals are sensed within a prescribed time period or time window, which is called atrial or ventricular escape interval, respectively, then the escape interval is reset (i.e., restarted) and generation of a stimulation pulse is inhibited and no unnecessary stimulation pulse is triggered. The escape interval is measured from the last heartbeat, i.e., from the last occurrence of an intrinsic (sensed) atrial event (P-wave, A-sense, AS) if the atrium is monitored, or an intrinsic (sensed) ventricular event (R-wave, V-sense, VS) if the ventricle is monitored, or the generation of a stimulation pulse (V-pace, VP; A-pace, AP) if no respective intrinsic event has occurred. If the escape interval "times-out", i.e., if a time period equal to the escape interval has elapsed without the sensing of a P-wave and/or R-wave (depending upon which chamber of the heart is being monitored), then a stimulation pulse is generated at the conclusion of the escape interval, and the escape interval is reset, i.e., restarted. In this way, the pacemaker provides stimulation pulses "on demand," i.e., only as needed, when intrinsic cardiac activity does not occur within the prescribed escape interval.

Several modes of operation are available in a state of the art multi mode pacemaker. The pacing modes of a pacemaker, both single and dual or more chamber pacemakers, are classified by type according to a three letter code. In such code, the first letter identifies the chamber of the heart that is paced (i.e., that chamber where a stimulation pulse is delivered), with a "V" indicating the ventricle, an "A" indicating the atrium, and a "D" indicating both the atrium and ventricle. The second letter of the code identifies the chamber wherein cardiac activity is sensed, using the same letters, and wherein an "O" indicates no sensing occurs. The third letter of the code identifies the action or response that is taken by the pacemaker. In general, three types of action or responses are recognized: (1) an Inhibiting ("I") response wherein a stimulation pulse is delivered to the designated chamber at the conclusion of the appropriate escape interval unless cardiac activity is sensed during the escape interval, in which case the stimulation pulse is inhibited; (2) a Trigger ("T") response wherein a stimulation pulse is delivered to a prescribed chamber of the heart a prescribed period of time after a sensed event; or (3) a Dual ("D") response wherein both the Inhibiting mode and Trigger mode may be evoked, e.g., with the "inhibiting" occurring in one chamber of the heart and the "triggering" in the other.

To such three letter code, a fourth letter "R" may be added to designate a rate-responsive pacemaker and/or whether the rate-responsive features of such a rate-responsive pacemaker are enabled ("O" typically being used to designate that rate-responsive operation has been disabled). A rate-responsive pacemaker is one wherein a specified parameter or combination of parameters, such as physical activity, the amount of oxygen in the blood, the temperature of the blood, etc., is sensed with an appropriate sensor and is used as a physiological indicator of what the pacing rate should be. When enabled, such rate-responsive pacemaker thus provides stimulation pulses that best meet the physiological demands of the patient.

Multiple-mode, demand-type, cardiac pacemakers shall allow a sequence of contractions of the heart's chamber which equals as far as possible a natural behavior of the healthy heart for damaged or diseased hearts that are unable to do so on their own.

In a healthy heart, initiation of the cardiac cycle normally begins with depolarization of the sinoatrial (SA) node. This specialized structure is located in the upper portion of the right atrium wall and acts as a natural "pacemaker" of the heart. In a normal cardiac cycle and in response to the initiating SA depolarization, the atrium contracts and forces the blood that has accumulated therein into the ventricle. The natural stimulus causing the atrium to contract is conducted to ventricle via the atrioventricular node (AV node) with a short, natural delay, the atrioventricular delay (AV-delay). Thus a short time after an atrial contraction (a time sufficient to allow the bulk of the blood in the atrium to flow through the one-way valve into the ventricle), the ventricle contracts, forcing the blood out of the ventricle to body tissue. A typical time interval between contraction of the atrium and contraction of the ventricle might be 180 ms; a typical time interval between contraction of the ventricle and the next contraction of the atrium might be 800 ms.

Thus, in a healthy heart providing proper AV-synchrony an atrial contraction (A) is followed a relatively short time thereafter by a ventricle contraction (V), that in turn is followed a relatively long time thereafter by the next atrial contraction and so on. Where AV synchrony exists, the heart functions very efficiently as a pump in delivering life-sustaining blood to body tissue; where AV synchrony is absent, the heart functions as an inefficient pump.

To mimic the natural behavior of a heart, a dual-chamber pacemaker, in conventional manner, defines a basic atrial escape interval (AEI) that sets the time interval for scheduling an atrial stimulation pulse. The atrial escape interval can be started by a ventricular event and end with an atrial event. A basic AV delay (AVD) or ventricular escape interval (VEI) sets the time interval or delay between an atrial event and a ventricular event. In such embodiment, AEI and AVD (or VEI) thus together define a length of a heart cycle which is reciprocal to the pacing rate at which stimulation pulses are generated and delivered to a patient's heart in the absence of sensed natural cardiac activity.

For the purpose of this application, a "ventricular event" may refer either a natural ventricular excitation (intrinsic ventricular event) which is sensed as an R-wave or a ventricular stimulation pulse (V-pulse, VP). Similarly, an atrial event shall refer to both, a P-wave or an atrial stimulation pulse (A-pulse, AP).

Since the atrial escape interval usually defines the time of delivery of a next scheduled atrial stimulation pulse, and since an atrial stimulation pulse may be timed from the latest ventricular event as well as from the latest atrial event, in some cases the atrial escape interval is an A-A interval.

One basic parameter of a heart stimulator's operation is stimulation rate. The stimulation rate is the V-V interval or the A-A interval the heart stimulator is applying. In modern heart stimulators the stimulation rate is often time variable in order to meet a hemodynamic demand of a patient that depends on the patient's physical activity. A hemodynamic sensor or activity sensor can be provided to adapt the actual stimulation rate to an actual hemodynamic demand. A heart stimulator allowing such rate adaption is called rate adaptive. Usually the actual stimulation rate is elevated compared to a base (minimum) stimulation rate. The base stimulation rate is applied whenever a patient is at rest. In order to mimic a natural circadian rhythm different base stimulation rates are provided for daytime (daytime base stimulation rate) when the patient is expected to be awake and night time when the patient is expected to sleep (nighttime stimulation rate).

Some parameters of an implantable medical device impact the lifestyle of a patient. An example is the time at which an implantable pulse generator (IPG) transitions from nighttime stimulation rate to daytime base stimulation rate. The former is generally lower than the later and thus provides less hemodynamic support. A pacemaker dependent person may thus feel less energetic if he or she wakes up before the programmed transition time.

All parameters may be programmed by the physician at follow-up using a device known as "physician programmer". The follow-ups typically occur every three to six months. The physician may not have the time to discuss all the lifestyle impacting parameters with the patient. Even if time is allocated to this task during the follow-up, adapting the parameters to the lifestyle of the patient only two to four times a year may not provide sufficient granularity to react to changes that can potentially occur daily.

BRIEF SUMMARY OF THE INVENTION

It is an object of the invention to provide a heart stimulator that best fits the need of a patient.

The fundamental idea to achieve the object of the invention consists in allowing the patient to modify a subset of implantable medical devices parameters.

According to the invention the patient can modify selected parameters of its implantable medical device that impact his or her lifestyle more often, thereby improving quality of life.

This is achieved by an implantable medical device (IMD) that can be wirelessly connected to a user interface by which a patient can enter values of selected control parameters for controlling the IMD whereas other control parameters are not accessible via said user interface and can only be modified by a physician or other authorized personnel.

The term selected parameter or selected control parameter shall apply to those parameters that a patient can change. Non-selected parameters thus are parameters that only can be changed by authorized personnel such as a physician.

The selected subset of implantable medical devices parameters that a patient can modify comprises only parameters, with associated tuning ranges, that may safely be changed by someone without medical training. For example, an average patient can be trusted to adapt the transition time of an IPG from nighttime rate to daytime rate to its lifestyle, much like he or she would program an alarm clock. On the other hand, changing the atrioventricular delay interval (AV delay interval) requires knowledge not found outside the expert community and this parameter should therefore not be available for the patient to modify.

According to the invention, the implantable medical device comprises a telemetry unit connected to a memory and a control unit that control the implantable medical device's operation according to parameters stored in the memory.

The telemetry unit is adapted to wirelessly receive parameters for controlling the implantable medical device.

It is part of the invention to define a subset of implantable medical devices parameters that can be changed and the ranges within these selected parameters that can be changed, and to define other parameters that only can be amended by a physician.

In addition to adapt the heart stimulator so as to allow some selected parameters to be manipulated by a patient, a user interface is provided allowing the patient to modify the selected subset of the implantable medical device's parameters that can be patient modified.

According to alternative preferred embodiments of the invention two options are provided.

According to a first embodiment, the external device is provided with an interface that allows the patient to only modify the selected parameters. This external device can connect wirelessly to the implantable medical device. Optionally, the external device may be connected to a network where patient changes can be logged and analyzed. Optionally, the network may be connected to a physician network access so that the physician can receive notices of the patient changes to the parameters and review change history.

According to an alternative embodiment it is suggested to allow the patient to program selected parameters through a network access, for example a PC connected to the internet. The network access may be provided by a central service center that can connect to the implantable medical device via the external device. The central service center may thus provide a remotely accessible user interface that allows a user to only amend selected parameters. The central service center may further provide a second user interface with restricted access so only authorized personnel can access the second user interface. Via the second user interface a physician can amend other, non-selected parameters. The access to the first user interface (the patient interface) may be restricted so as to only allow a particular patient to access this interface in order to amend selected parameters of his own implantable medical device.

According to a particularly preferred embodiment according to the first alternative, the external device provides a wireless link to the implantable medical device and provides a user interface corresponding to a user interface of an alarm clock. In a particularly preferred embodiment, the external device is adapted to allow the patient to set the current time, program the wake-up alarm time and arm the wake-up alarm.

It is further preferred, that the external device is adapted to telemetrically instruct the implantable medical device to start the transition to nighttime rate when the patient arms the wake-up alarm. In addition, the external device may be adapted to telemetrically instruct the implantable medical device to program the wake-up alarm time that the patient entered as the transition time from nighttime rate to daytime rate.

Optionally, the external device may be connected to a central service center via a network where patient changes can be logged and analyzed. Optionally, the central service center provides a physician network access so that a physician can receive notices of the patient changes to the selected parameters and review change history.

Optionally, the external device may provide other features found in alarm clocks, such as a radio tuner and/or a CD player.

According to the invention this objective is achieved by a heart stimulation system comprising an implantable heart stimulator and an external transceiver device for wireless communication with said implantable heart stimulator.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
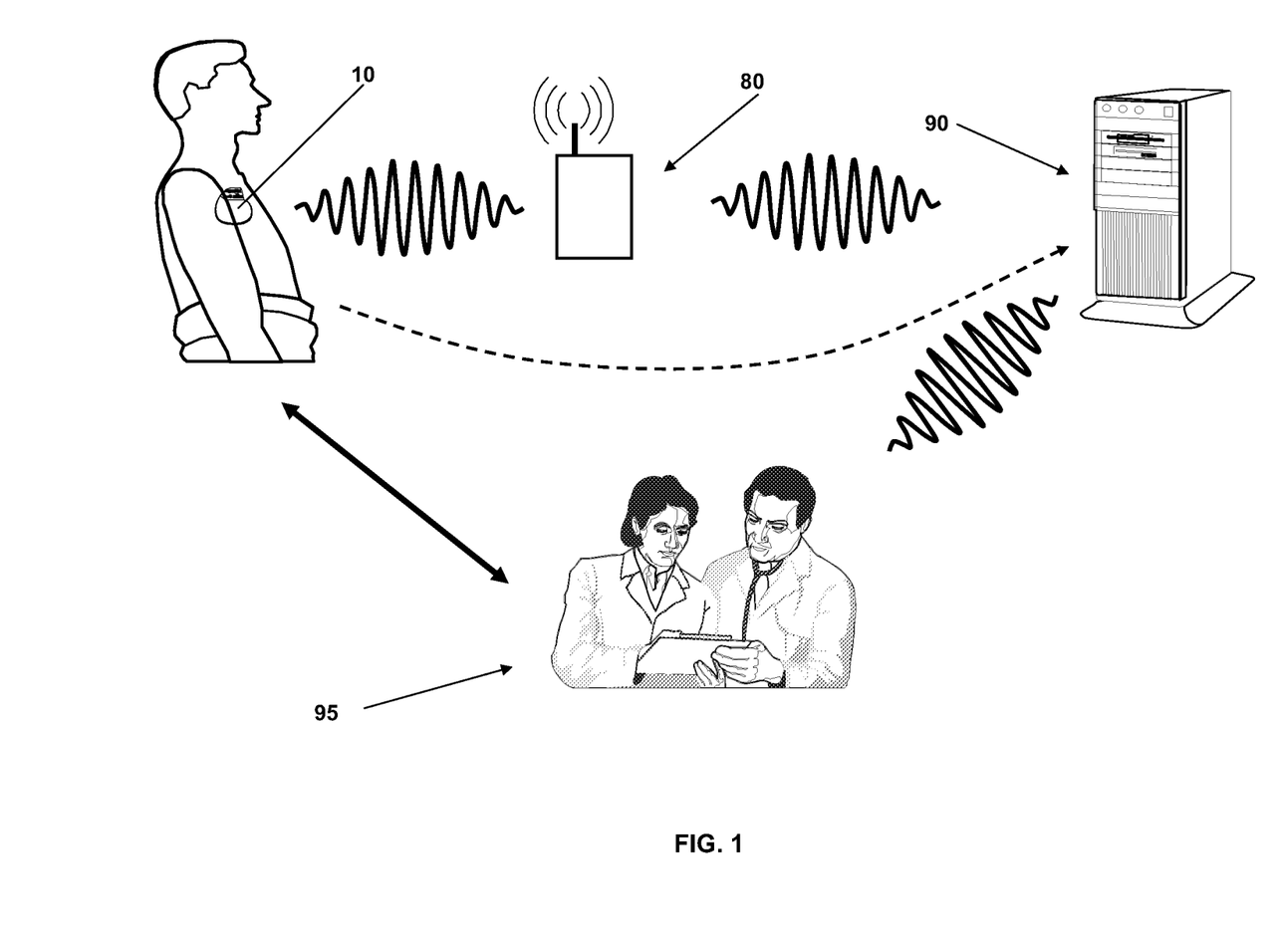
FIG. 1 is a schematic overview over a implantable device system comprising an implantable medical device, an external transceiver device and a service center.

FIG. 1 shows an implantable device system comprising an implantable medical device 10, an external transceiver device 80 and a central service center 90. The implantable medical device 10 is for example an implantable pacemaker or an implantable cardioverter/defibrillator or device for cardiac resynchronization. The implantable medical device 10 comprises an implant transceiver (not shown) for wireless communication with the external transceiver device 80. The external transceiver device 80 comprises an external transceiver unit (not shown) for wireless communication with the implant transceiver unit and a data communication interface (also not shown) adapted to allow a data communication with the service center 90. The data communication interface preferably is adapted to use a public data communication line as a telephone landline connection or wireless connection via GPRS/UMTS or SMS.

The central service center 90 comprises or is connected to a user interface allowing a physician or a team of physicians to interact with the central service center. The user interface may comprise a display for displaying data to the physician 100 and some input device allowing the physician 95 to enter instructions or data into the central service center 90. The central service center 90 further comprises a central data base that is connected to said data communication interface (see FIG. 4) and a data evaluation module that is connected to the data base that is adapted to evaluate data stored in said data base.

Figure 4:
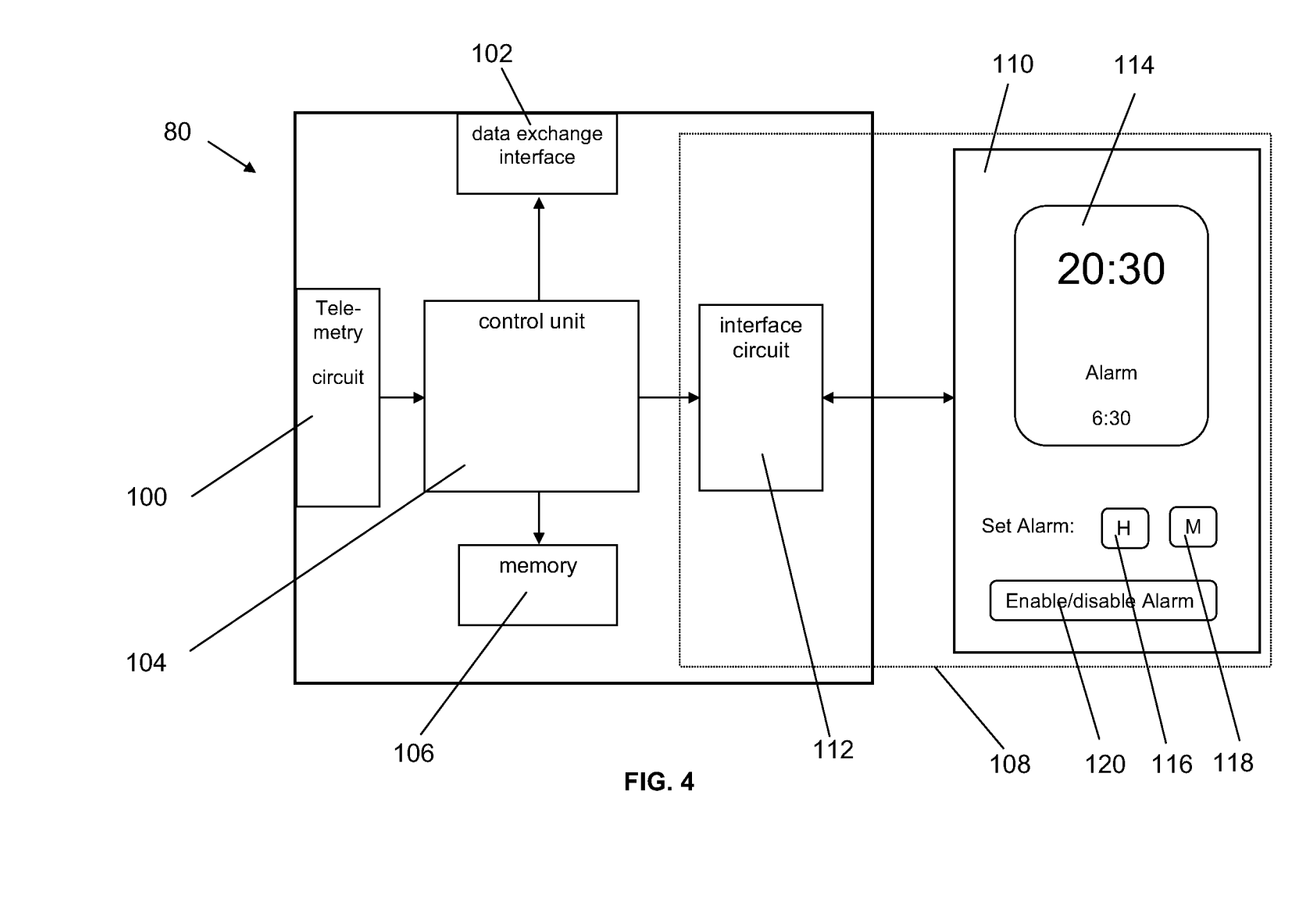
FIG. 4 is a schematic diagram of the external transceiver device.

A patient having the medical device 10 implanted may communicate with the implantable medical device 10, the central service center 90 or both by means of the external transceiver device 80. For this purpose, the external transceiver device 80 may feature a user interface 108 as is illustrated in FIG. 4. The patient may also directly connect with the central service center 90 without using the external device but via the internet, for example.

Figure 2:
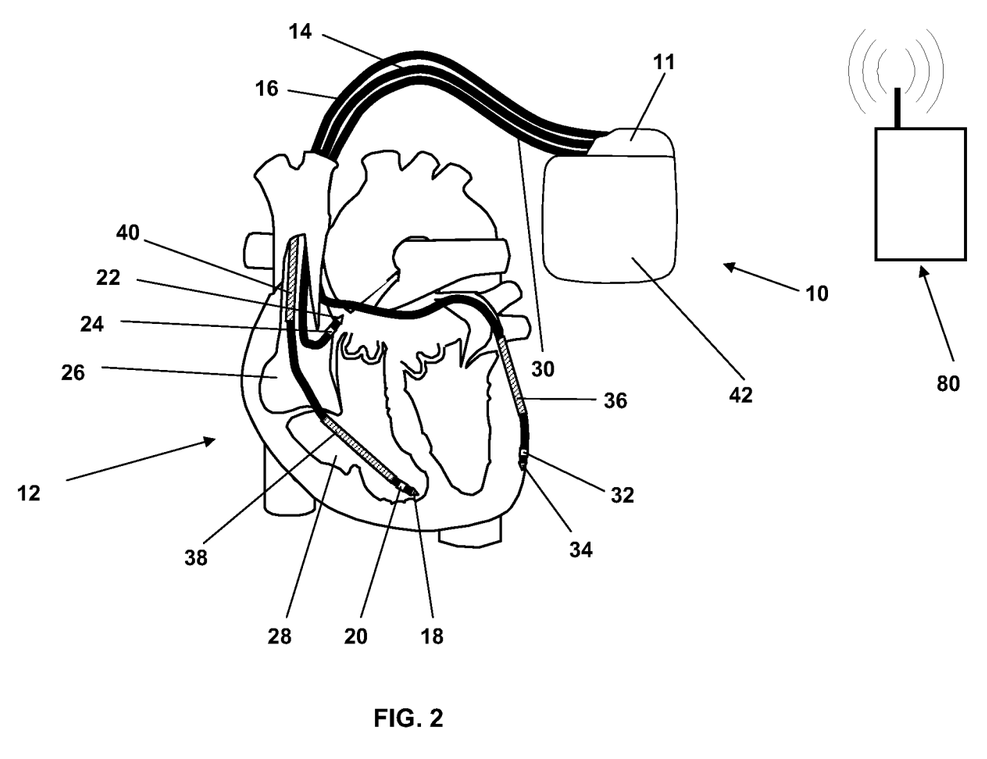
FIG. 2 shows a three chamber bi-ventricular implantable cardioverter/defibrillator (ICD).

In FIG. 2 the implantable medical device is a three chamber biventricular pacemaker and cardioverter/defibrillator 10 that is connected to pacing/sensing leads placed in a heart 12 is illustrated.

Pacemaker 10 comprises a gas proof housing (case) 42 made from a biocompatible metal such as titanium. Pacemaker 10 comprises a transparent header 11 that is made from electrically insulating plastic and that encloses terminals to which electrode leads 16, 18 and 30 are connected detachably. Electrode leads 16, 18 and 30 each comprise a proximal connector (not shown) that is plugged into the connectors of header 13.

The implantable medical device 10 is electrically coupled to heart 12 by way of leads 14, 16 and 30.

Lead 14 is a right atrial electrode lead that has a pair of right atrial electrodes 22 and 24 that are in contact with the right atria 26 of the heart 12.

Lead 16 is a right ventricular electrode lead that has a pair of ventricular stimulation and sensing electrodes 18 and 20 that are in contact with the right ventricle 28 of heart 12. Further, a ventricular defibrillation shock coil 38 and an atrial defibrillation shock coil 40 are arranged on lead 16.

Electrodes 22 and 18 are tip electrodes at the very distal end of leads 14 and 16, respectively. Electrode 22 is a right atrial tip electrode RA Tip and electrode 18 is a right ventricular tip electrode. Electrodes 24 and 20 are ring electrodes in close proximity but electrically isolated from the respective tip electrodes 22 and 18. Electrode 24 forms a right atrial ring electrode RA Ring and electrode 20 forms a right ventricular ring electrode RV Ring. Atrial cardioversion shock coil 40 is a coil electrode providing a relatively large geometric area when compared to the stimulation electrodes 18, 20, 22 and 24.

Lead 30 is a left ventricular electrode lead passing through the coronary sinus of heart 12 and having a left ventricular ring electrode LV RING 32 a left ventricular tip electrode LV TIP 34. Further, a left ventricular defibrillation shock coil 36 is arranged on lead 30.

Implantable medical device 10 has a case 42 made from electrically conductive material such as titanium that can serve as a large surface electrode IMD CASE.

The plurality of electrodes 18, 20, 22, 24, 32, 34, 36, 38 and 40 connected to implantable medical device 10 together with case 42 allow for a number of different electrode configurations for measuring intrathoracic and intracardiac impedance.

Figure 3:
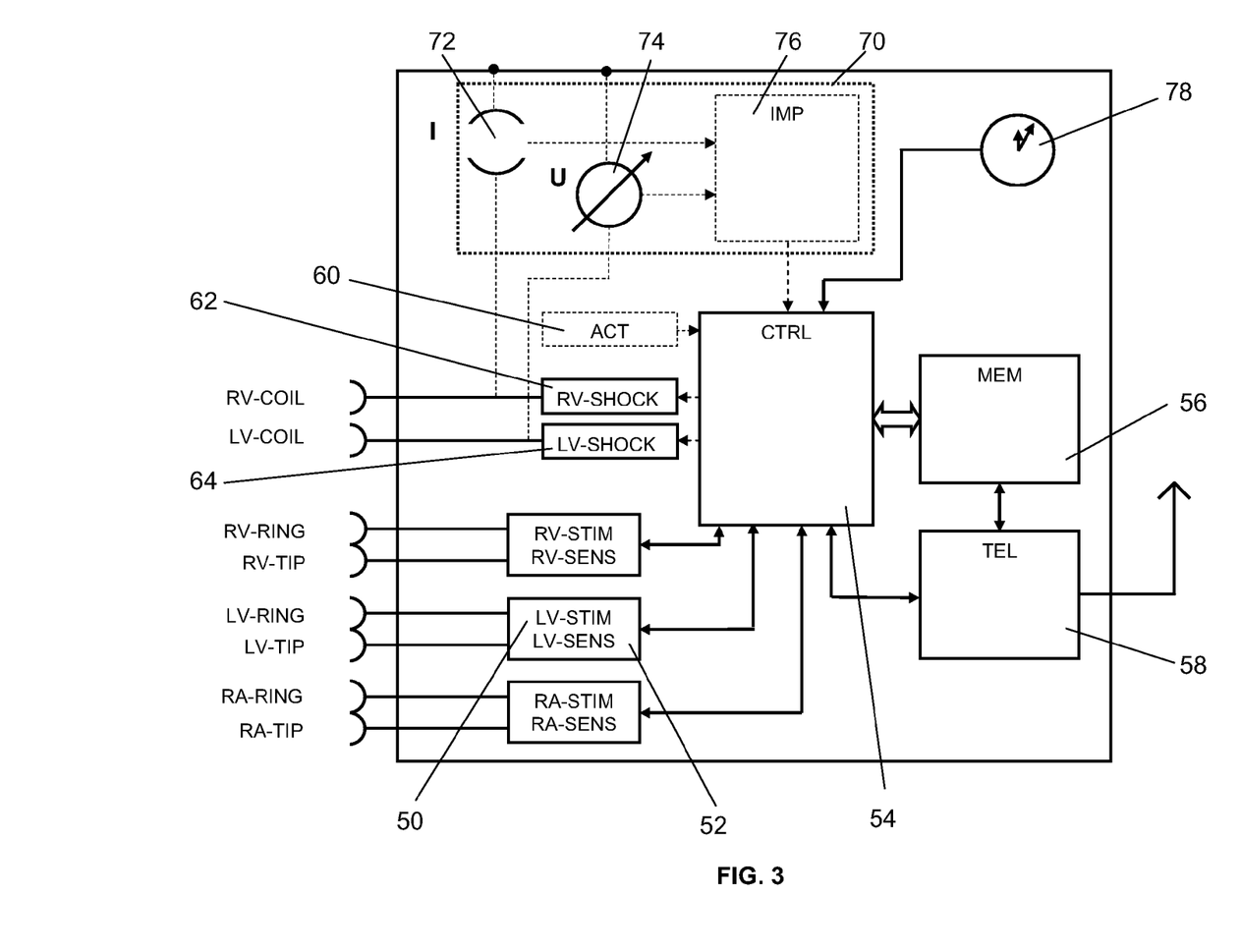
FIG. 3 is a schematic diagram of the device modules of the ICD of FIG. 2.

Referring to FIG. 3 a simplified block diagram of an implantable medical device 10 is illustrated. During operation of the pacemaker leads 14, 16 and 30 are connected to respective output/input terminals of pacemaker 10 as indicated in FIG. 2 and carry stimulating pulses to the tip electrodes 18, 22 and 34 from a right ventricular pulse generator RV-STIM, a right atrial stimulation pulse generator RA-STIM and a left ventricular pulse generator LV-STIM, respectively. Further, electrical signals from the right ventricle are carried from the electrode pair 18 and 20, through the lead 16, to the input terminal of a right ventricular sensing stage RV-SENS; and electrical signals. from the right atrium are carried from the electrode pair 22 and 24, through the lead 14, to the input terminal of a right atrial channel sensing stage RA-SENS. Electrical signals from the left ventricle are carried from the electrode pair 32 and 34, through the lead 30, to the input terminal of a right ventricular sensing stage RV-SENS The atrial channel sensing stage A-SENS and ventricular sensing stages RV-SENS and LV-SENS comprise analog to digital converter (ADC; not shown) that generate a digital signal from electric signals picked up in the atrium or the ventricle, respectively.

Controlling the implantable medical device 10 is a control unit CTRL 54 that is connected to sensing stages A-SENS and V-SENS, to stimulation pulse generators A-STIM and V-STIM and to an impedance determination unit 70. Control unit CTRL 54 comprises a digital microprocessor forming a central processing unit (CPU; not shown) and is—at least in part—controlled by a program stored in a memory circuit MEM 56 that is coupled to the control unit CTRL 54 over a suitable data/address bus ADR.

Control unit CTRL 54 receives the output signals from the atrial sensing stage RA-SENS and from the ventricular sensing stages RV-SENS and LV-SENS. The output signals of sensing stages RA-SENS and RV-SENS are generated each time that a P-wave representing an intrinsic atrial event or an R-wave representing an intrinsic ventricular event, respectively, is sensed within the heart 12. An As-signal is generated, when the atrial sensing stage RA-SENS detects a P-wave and a Vs-signal is generated, when the ventricular sensing stage RV-SENS detects an R-wave.

Control unit CTRL 54 also generates trigger signals that are sent to the atrial stimulation pulse generator RA-STIM and the ventricular stimulation pulse generators RV-STIM and LV-STIM, respectively. These trigger signals are generated each time that a stimulation pulse is to be generated by the respective pulse generator RA-STIM, RV-STIM or LV-STIM. The atrial trigger signal is referred to simply as the "A-pulse", and the ventricular trigger signal is referred to as the "V-pulse". During the time that either an atrial stimulation pulse or ventricular stimulation pulse is being delivered to the heart, the corresponding sensing stage, RA-SENS, RV-SENS and/or LV-SENS, is typically disabled by way of a blanking signal presented to these amplifiers from the control unit CTRL 54, respectively. This blanking action prevents the sensing stages RA-SENS, RV-SENS and LV-SENS from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Furthermore, atrial sense events As recorded shortly after delivery of a ventricular stimulation pulses during a preset time interval called post ventricular atrial refractory period (PVARP) are generally recorded as atrial refractory sense event Ars but ignored.

Control unit CTRL 54 comprises circuitry for timing ventricular and/or atrial stimulation pulses according to an adequate stimulation rate that can be adapted to a patient's hemodynamic need as pointed out below.

Control unit CTRL 54 is connected to a memory circuit MEM 56 that allows certain control parameters, used by the control unit CTRL 54 in controlling the operation of the implantable medical device 10, to be programmably stored and modified, as required, in order to customize the implantable medical device's operation to suit the needs of a particular patient. Such data includes the basic timing intervals used during operation of the pacemaker 10 and AV delay values and hysteresis AV delay values in particular. The stored control parameters in particular include an AV delay interval, a daytime base stimulation rate, a nighttime base stimulation rate and a night-to-day transition time and a day-to-night transition time.

Further, data sensed during the operation of the implantable medical device 10 may be stored in the memory MEM 56 for later retrieval and analysis.

A telemetry circuit TEL 58 is further included in the implantable medical device 10. This telemetry circuit TEL 58 is connected to the control unit CTRL 54 by way of a suitable command/data bus. Telemetry circuit TEL 58 allows for wireless data exchange between the implantable medical device 10 and some remote programming or analyzing device which can be part of a centralized service center serving multiple pacemakers. Telemetry circuit 56 serves as a data interface for wireless data communication with external device 80 and for receiving values for selected control parameters to be stored in memory circuit MEM 56, in particular. The selected control parameters include the night-to-day transition time and a day-to-night transition time.

The implantable medical device 10 in FIG. 3 is referred to as a three chamber pacemaker/cardioverter/defibrillator because it interfaces with the right atrium 26, the right ventricle 28 and the left ventricle of the heart 12. Those portions of the pacemaker 10 that interface with the right atrium, e.g., the lead 14, the P-wave sensing stage A-SENSE, the atrial stimulation pulse generator A-STIM and corresponding portions of the control unit CTRL 54, are commonly referred to as the atrial channel. Similarly, those portions of the pacemaker 10 that interface with the right ventricle 28, e.g., the lead 16, the R-wave sensing stage V-SENSE, the ventricular stimulation pulse generator V-STIM, and corresponding portions of the control unit CTRL 54, are commonly referred to as the ventricular channel.

In order to be able to detect periods of physical activity of a patient indicating that the patient is awake and in order to allow rate adaptive pacing in a DDDR or a DDIR mode, the pacemaker 10 further includes a physiological sensor ACT 60 that is connected to the control unit CTRL 54 of the pacemaker 10. While this sensor ACT 60 is illustrated in FIG. 2 as being included within the pacemaker 10, it is to be understood that the sensor may also be external to the implantable medical device 10, yet still be implanted within or carried by the patient.

The control unit CTRL 54 is adapted to determine an adequate heart rate or stimulation rate in any manner known as such. This includes application of a base application when a patient is at rest and applying an elevated stimulation rate, when the activity sensor 60 senses physical activity of a patient. Depending on the daytime, either a daytime base stimulation rate is applied or a nighttime base stimulation rate.

For impedance measurement, impedance determination unit 70 is provided. Impedance determination unit 70 comprises a constant current source 72 that is connected or can be connected to electrodes for intracorporeal placement as shown in FIG. 2. In order to allow for a plurality of impedance measurement electrode configurations, preferably some means of switching is provided between the constant current source 72 and the electrode terminals of the implantable medical device 10. The switch is not shown in FIG. 3. Rather, particular impedance measurement configurations are shown as examples.

Similarly, a impedance measuring unit 74 for measuring a voltage corresponding to a current fed through a body by said constant current source is provided and can be connected to a number of electrodes although a switch for switching between these configurations is not shown in FIG. 3.

As an alternative to constant current source 72 a constant voltage source can be provided. Then, the measuring unit will be adapted to measure a current strength of a current fed through a body by said constant voltage source.

Both, constant current source 72 and impedance measurement unit 74, are connected to an impedance value determination unit 76 that is adapted to determine an impedance value for each measuring current pulse delivered by the constant current source 72.

The impedance value determination unit 76 comprises another analog to digital converter ADC in order to generate a digital impedance signal that is fed to the control unit CTRL 54.

Further, a clock 78 is connected to control unit CTRL 54 in order to allow control unit 54 to control a base stimulation depending on the daytime. Depending on the output signal of clock 78 and the night-to-day transition time and a day-to-night transition time stored in Memory circuit 56, control unit CTRL 54 either applies the daytime base stimulation rate or the nighttime base stimulation rate as stored in memory circuit MEM 56.

Control unit CTRL 54 further comprises watchdog and reset units to provide safety when the CPU should fail. The watchdog units therefore are designed to operate independently from the CPU of the control unit CTRL 54. In FIG. 3, the watchdog and reset units are not shown.

FIG. 4 is a more detailed representation of the external transceiver device 80. The external device 80 comprises a telemetry circuit 100 adapted for wireless data transmission to the implantable medical device 10 and a data exchange interface 102 adapted to allow a data communication with service center 90. Both, the telemetry circuit 100 and the data exchange interface 102 are connected to an external device control unit 104. The external device control unit 104 is connected to an external device memory 106. The external device memory 106 is adapted to store data received from or to be transmitted to either the central service center 90 or to the implant 10. Further, the external device memory circuit 106 comprises data that can be entered via an external device user interface 108. The external device user interface 108 is connected to the external device control unit 104 and comprises an input and display panel 110 and an interface circuit 112. The input display panel 110 comprises a display 114 and two input buttons 116 and 118.

The user interface 108 is adapted to display an actual day time on the display 114. Further, an alarm time can be set via buttons 116 and 118. Button 116 serves for entering the hour of alarm and button 118 serves for entering the minute of alarm. The alarm time thus set is displayed in display 114. In order to enable or disable the alarm a toggle-button 120 is provided. The state of the alarm—enabled or disabled—is indicated on display 114 by an according icon.

Control unit 104 of the external device 80 is adapted to generate a data package to be sent to implant 10, whenever an alarm is activated via user interface 108. The data package comprises a night to day transition time corresponding to the alarm time set via user interface 108 and a day to night transition time corresponding to the actual day time when the alarm was activated.

This data package is received by telemetry circuit 58 of the implantable medical device 10 and the night to day transition time and the day to night transition time contained in the data package is stored in memory circuit MEM 56 of the implantable medical device 10. The selected parameters thus generated, transmitted and stored in the implantable medical device 10 are used as control parameters for controlling the implantable medical device via the implantable medical device control unit CTRL 54.

Although an exemplary embodiment of the present invention has been shown and described, it should be apparent to those of ordinary skill that a number of changes and modifications to the invention may be made without departing from the spirit and scope of the invention. This invention can readily be adapted to a number of different kinds of implantable medical devices by following the present teachings. All such changes, modifications and alterations should therefore be recognized as falling within the scope of the present invention.

What is claimed is:

1. A heart stimulation system comprising:
   a memory;
   a control unit connected to said memory;
   said control unit configured to control operation of an implantable medical device with control parameters stored in said memory;

said control parameters comprising
  parameters that may only be modified by a physician or other authorized personnel, and
  selected parameters comprising a subset of said control parameters with associated tuning ranges that are safe for a user to modify and that may also be modified by said physician or said other authorized personnel, wherein said physician or said other authorized personnel is not said user and wherein said implantable medical device is located within said user and not within said physician or said other authorized personnel;
a data interface connected to said memory, wherein said data interface is configured to receive said control parameters and store said control parameters in said memory;
an external device;
a first user interface on said external device, wherein said first user interface is at least indirectly coupled to said data interface; and,
  wherein said first user interface on said external device is configured to
    allow said user to enter values for said selected parameters comprising the subset of said control parameters that are safe for said user to modify, and allow said user to only modify said selected parameters,
    not allow said user to modify said parameters that may only be modified by a physician or other authorized personnel who are not said user; and,
    accept night-to-day transition and day-to-night transition times, and assert an alarm on said external device to wake said user; and,
a second user interface at least indirectly coupled to said external device;
wherein said second user interface comprises restricted access to only allow said physician or other authorized personnel who are not said user to access said second user interface to modify said control parameters that may only be modified by a physician or other authorized personnel who are not said user;
wherein said control parameters that may only be modified by said physician or other authorized personnel who are not said user include an AV delay interval, a daytime base stimulation rate, and a nighttime base stimulation rate; and,
wherein the selected parameters that may be modified by said user and that may also be modified by said physician or said other authorized personnel comprise said night-to-day transition and said day-to-night transition times.

2. The system according to claim 1, further comprising:
a first telemetry unit configured to wirelessly communicate with said external device; and,
wherein said data interface is part of said first telemetry unit.

3. The system according to claim 2, wherein said first user interface is part of said external device, said external device further comprising a second telemetry unit for wireless data communication with said first telemetry unit, wherein said second telemetry unit is coupled with said first user interface.

4. The system according to claim 1,
wherein said implantable medical device is an implantable heart stimulator.

5. The system of claim 4 further comprising:
a first telemetry unit in said implantable medical device that is configured to wirelessly communicate with said external device;
wherein said data interface is part of said first telemetry unit that is configured to wirelessly communicate with said external device;
said external device further comprising a second telemetry unit for wireless data communication with said first telemetry unit of said implantable medical device, said second telemetry unit being at least indirectly connected to said first user interface; and,
wherein said external device is configured to transmit said night-to-day transition and said day-to-night transition times to said first telemetry unit of said implantable medical device and store said set night-to-day transition and day-to-night transition times in said memory.

6. The system of claim 5 further comprising:
a service center configured to communicate with said implantable heart stimulator;
  wherein said second user interface is part of said service center and is remotely accessible;
  said external device further configured to wirelessly communicate with said implantable heart stimulator and said service center; and,
  wherein said service center provides a remotely accessible third user interface that is configured to allow said user to set said selected parameters to control said implantable heart stimulator.

7. A system comprising: an external device comprising:
a first user interface;
a control unit;
said external device configured to wirelessly communicate control parameters to an implantable medical device comprising a first telemetry unit;
said control parameters comprising
  parameters that may only be modified by a physician or other authorized personnel, and
  selected parameters comprising a subset of said control parameters with associated tuning ranges that are safe for a user to modify and that may also be modified by said physician or said other authorized personnel, wherein said physician or said other authorized personnel is not said user and wherein said implantable medical device is located within said user and not within said physician or said other authorized personnel;
a second telemetry unit for wireless data communication with said first telemetry unit of said implantable medical device;
said second telemetry unit being at least indirectly connected to said first user interface;
wherein said first user interface is configured to
  allow said user to enter values for said selected parameters comprising the subset of said control parameters that are safe for said user to set, and allow said user to only modify said selected parameters,
  not allow said user to modify said parameters that may only be modified by a physician or other authorized personnel who are not said user, and
  accept night-to-day transition and day-to-night transition times and assert an audio alarm on said external device to wake said user;
wherein said control unit is configured to generate a data packet to be transmitted to said implantable medical device after said user has entered values of said selected parameters via said first user interface;
wherein said external device is further configured to instruct said implantable medical device to start a transition to a nighttime rate when said user arms a wake-up alarm on said external device;

wherein said external device is further configured to instruct said implantable medical device to program a wake-up alarm time that said user has entered in said first user interface on said external device as said night-to-day transition time;

wherein said external device is further configured to at least indirectly couple with a second user interface;

wherein said second user interface comprises restricted access to only allow said physician or other authorized personnel who are not said user to access said second user interface to modify said control parameters that may only be modified by a physician or other authorized personnel who are not said user;

wherein said control parameters that may only be modified by said physician or other authorized personnel who are not said user include an AV delay interval, a daytime base stimulation rate, and a nighttime base stimulation rate; and, wherein the selected parameters that may be modified b said user and that may also be modified by said physician or said other authorized personnel comprise said night-to-day transition and said day-to-night transition times.

8. The system of claim 7 wherein said external device is further configured to couple to a network and log selected parameters set by said user to said network for review by said physician or said other authorized personnel.

9. The system of claim 7 wherein said external device comprises a radio tuner.

10. The system of claim 7 wherein said external device comprises a CD Player.

11. The system of claim 7 further comprising a service center;
wherein said second user interface is part of said service center and is remotely accessible; and,
wherein said service center provides a remotely accessible third user interface that is configured to
allow said physician or said other authorized personnel who are not said user to set parameters that may only be modified by said physician or said other authorized personnel and
allow said user or said physician or said other authorized personnel who are not said user to also set said selected parameters comprising the subset of said control parameters that are safe for said user to set.

12. A heart stimulation system comprising:
an implantable medical device comprising
a memory;
a control unit connected to said memory;
said control unit configured to control operation of said implantable medical device with control parameters stored in said memory;
said control parameters comprising
parameters that may only be modified by a physician or other authorized personnel, and
selected parameters comprising a subset of said control parameters with associated tuning ranges that are safe for a user to modify and that may also be modified by said physician or said other authorized personnel, wherein said physician or said other authorized personnel is not said user, and wherein said implantable medical device is located within said user and not within said physician or said other authorized personnel;
a data interface connected to said memory wherein said data interface is configured to receive said control parameters and store said control parameters in said memory;
a first telemetry unit that is part of said data interface;
an external device comprising
a first user interface configured to
allow said user to enter values for said selected parameters comprising the subset of said control parameters that are safe for said user to set, and
not allow said user to modify said control parameters that may only be modified by a physician or other authorized personnel who are not said user;
an alarm;
a second telemetry unit for wireless data communication with said first telemetry unit of said implantable medical device, said second telemetry unit being at least indirectly connected to said first user interface;
wherein said first user interface is further configured to allow said user to set a night-to-day transition and a day-to-night transition times and wherein said external device is configured to transmit said night-to-day transition and said day-to-night transition times to said first telemetry unit of said first telemetry unit of said implantable medical device and store said set night-to-day transition and day-to-night transition times in said memory;
wherein said external device is configured to assert said alarm on said external device to wake said user;
a service center configured to
communicate with said implantable medical device and said external device;
provide a second user interface that is remotely accessible;
provide a remotely accessible third user interface that is configured to allow said user to set said selected parameters to control said implantable heart stimulator, said selected parameters comprising the subset of said parameters that are safe for said user to set, and wherein said third user interface does not allow said user to modify said control parameters that may only be modified by a physician or other authorized personnel;
wherein said third remotely accessible user interface is configured to allow said physician or said other authorized personnel to set parameters that may only be modified by said physician or said other authorized personnel and also set said selected parameters comprising the subset of said parameters that are safe for said user to set;
wherein said second remotely accessible user interface comprises restricted access to only allow said physician or other authorized personnel who are not said user to access said second user interface to modify said control parameters that may only be modified by a physician or other authorized personnel who are not said user;
wherein said control parameters that may only be modified by said physician or other authorized personnel who are not said user include an AV delay interval, a daytime base stimulation rate, and a nighttime base stimulation rate; and,
wherein the selected parameters that may be modified b said user and that may also be modified by said physician or said other authorized personnel comprise said night-to-day transition and said day-to-night transition times.

13. The system of claim 12 wherein said external device is further configured to couple to a network and log selected parameters set by said user to said network for review by said physician or said other authorized personnel.

14. The system of claim 12 wherein said external device is further configured to instruct said implantable medical device to start a transition to a nighttime rate when said user arms a wake-up alarm.

15. The system of claim 12 wherein said external device is further configured to instruct said implantable medical device to program a wake-up alarm time that said user has entered in said first user interface as said night-to-day transition time.

16. The system of claim 12 wherein said external device comprises a radio tuner.

17. The system of claim 12 wherein said external device comprises a CD Player.

\* \* \* \* \*